US006544777B1

(12) United States Patent
Schrenzel et al.

(10) Patent No.: US 6,544,777 B1
(45) Date of Patent: Apr. 8, 2003

(54) NON-COGNATE HYBRIDIZATION SYSTEM (NCHS)

(76) Inventors: Jacques Schrenzel, 1 chemin des Tulipiers, CH-1208 Geneva (CH); Jonathan Hibbs, 116 Pinehurst Ave., Albany, NY (US) 12203

( * ) Notice: Subject to any disclaimer, the term of this patent is extended or adjusted under 35 U.S.C. 154(b) by 0 days.

(21) Appl. No.: 09/586,101

(22) Filed: Jun. 2, 2000

Related U.S. Application Data

(60) Provisional application No. 60/137,327, filed on Jun. 3, 1999.

(51) Int. Cl.$^7$ ............ C12Q 1/68; C12P 19/34; C12M 1/34; C07H 21/02; C07H 21/04
(52) U.S. Cl. ............ 435/287.2; 435/6; 435/91.1; 435/91.2; 435/286.5; 435/402; 536/22.1; 536/23.1; 536/24.3; 536/24.31; 536/24.32; 536/24.33; 436/518
(58) Field of Search ............ 435/6, 91.1, 5, 435/286.5, 287.2, 402; 536/25.3, 24.3, 24.32, 24.33, 22.1; 436/518

(56) References Cited

U.S. PATENT DOCUMENTS

| | | | |
|---|---|---|---|
| 5,556,752 A | | 9/1996 | Lockhart et al. ............... 435/6 |
| 5,578,832 A | | 11/1996 | Trulson et al. ................. 435/6 |
| 5,593,839 A | | 1/1997 | Hubbell et al. ................ 435/6 |
| 5,631,734 A | | 5/1997 | Stern et al. .................. 356/317 |
| 5,700,637 A | * | 12/1997 | Southern ....................... 435/6 |
| 5,733,729 A | | 3/1998 | Lipshutz et al. ............... 435/6 |
| 5,744,305 A | | 4/1998 | Fodor et al. ................... 435/6 |
| 5,770,456 A | | 6/1998 | Holmes ....................... 436/518 |
| 5,770,722 A | | 6/1998 | Lockhart et al. ........... 536/25.2 |
| 5,795,714 A | * | 8/1998 | Cantor et al. .................. 435/6 |
| 5,807,522 A | * | 9/1998 | Brown et al. ................. 422/50 |
| 5,834,758 A | | 11/1998 | Trulson et al. ........... 250/201.2 |
| 5,837,832 A | | 11/1998 | Chee et al. ................ 536/22.1 |
| 5,843,655 A | | 12/1998 | McGall ......................... 435/6 |
| 5,856,101 A | | 1/1999 | Hubbell et al. .......... 435/286.5 |
| 5,858,659 A | | 1/1999 | Sapolsky et al. ............... 435/6 |
| 5,861,242 A | * | 1/1999 | Chee et al. .................... 435/5 |
| 5,874,219 A | | 2/1999 | Rava et al. .................... 435/6 |
| 5,885,837 A | | 3/1999 | Winkler et al. ............. 435/91.1 |
| 5,919,523 A | | 7/1999 | Sundberg et al. ........... 427/333 |
| 5,922,591 A | * | 7/1999 | Anderson et al. ........ 435/287.2 |
| 5,925,525 A | * | 7/1999 | Fodor et al. ................... 435/6 |
| 5,974,164 A | | 10/1999 | Chee ......................... 382/129 |
| 5,981,185 A | * | 11/1999 | Matson et al. ................. 435/6 |
| 6,268,128 B1 | * | 7/2001 | Collins et al. ................. 435/6 |

FOREIGN PATENT DOCUMENTS

| | | |
|---|---|---|
| EP | 0 785 280 A | 7/1997 |
| WO | WO94 19480 A | 9/1994 |
| WO | WO95 00530 A | 1/1995 |
| WO | WO97 29212 A | 8/1997 |
| WO | WO98 15651 A | 4/1998 |
| WO | WO98 15652 A | 4/1998 |
| WO | WO99 28505 A | 6/1999 |

OTHER PUBLICATIONS

Walton et al. Creation of Stable Poly (ethylene Oxide) surfaces on poly (methy methacrylate) using blends of branched and linear polymers. Macromolecules. vol. 30, pp. 6947–6956, Nov. 1997.*
Shchepinov et al. Steric factors influencing hybridization of nucleic acids to oligonucleotide arrays. Nucleic acids Research. vol. 25, No. 6, pp. 1155–1161, May 1997.*
Gennady Yershov, et al., "DNA analysis and diagnostics on oligonucleotide microchips," Proc. Natl. Acad. Sci. USA, vol. 93, pp. 4913–4918, May 1996.
Dmitry Guschin, et al., "Manual Manufacturing of Oligonucleotide, DNA, and Protein Microchips," Analytical Biochemistry 250, 203–211 (1997) Article No. AB972209.
"Tricorders, Yactograms and the Future of Analytical Chemistry, When 'Nano–' Isn't Small Enough."
E.M. Southern, et al., "Analyzing and Comparing Nucleic Acid Sequences by Hybridization to Arrays of Oligonucleotides: Evaluation Using Experimental Models," Genomics 13, 1008–1017 (1992).
David D.L. Bowtell, "Options available—from start to finish—for obtaining expression data by microarray," nature genetics supplement, vol. 21, Jan., 1999.
Douglas E. Basset Jr., et al., "Gene expression informatics—it's all in your mine," nature genetics supplement, vol. 21, Jan., 1999.
Patrick O. Brown, et al., "Exploring the new world of the genome with DNA microarrays," nature genetics supplement, vol. 21, Jan., 1999.
William Bains, et al., "A Novel Method for Nucleic Acid Sequence Determination," J. theor. Biol. 135, 303–307 (1988).
Caviani Pease, Ann, et al. "Light–generated oligonucleotide arrays for rapid DNA sequence analysis." *Proceedings of the National Academy of Sciences, USA* 91 (May 1994): 5022–5026.

* cited by examiner

Primary Examiner—Jeffrey Siew
(74) Attorney, Agent, or Firm—Patterson, Thuente, Skaar & Christensen, P.A.

(57) ABSTRACT

The present invention comprises a non-cognate hybridization system (NCHS). The NCHS generally includes a hybridization technology that is simply and economically used to probe for non-cognate nucleic acid sequences, i.e., for nucleic acid strands without known target sequences. NCHS causes nucleic acids, bound to a probe surface, to create a hybridization pattern that provides information about the presence and/or quantity of the nucleic acid sequences in a sample. The NCHS results normally orient the examiner towards a small number of specific diagnoses across a wide variety of diagnostic categories (including but not limited to infections, neoplasms and autoimmune diseases). The test will also identify final-common-pathway syndromes such as sepsis, anaphylaxis and tumor necrosis. While the test utilizes genetic information, it does not depend on prior knowledge of the genes involved in a particular disease or syndrome.

30 Claims, 3 Drawing Sheets

PATTERNS ON A 15-MER CHIP

GENES DETECTED (%)

GENES SPECIFICALLY DETECTED (%)

PATTERNS ON A 16-MER CHIP

GENES DETECTED (%)

GENES SPECIFICALLY DETECTED (%)

NON-COGNATE HYBRIDIZATION SYSTEM (NCHS)

CROSS-REFERENCES TO RELATED APPLICATIONS

This application claims priority to and incorporates by reference the entire contents of U.S. Provisional Application No. 60/137,327 filed Jun. 3, 1999.

BACKGROUND OF THE INVENTION

Rapid, accurate diagnosis of acutely ill patients is critical for their survival. Typically, thousands of dollars in diagnostic tests are performed within 24 hours of a patient's admission to hospital. Accurate diagnosis of a treatable condition allows appropriate therapy to be started and unnecessary, potentially harmful medications to be stopped. On the other hand, some diagnostic tests require days to complete, some are invasive or even dangerous to perform, and all contribute to the upward spiral of medical costs. Selection and interpretation of appropriate tests in the appropriate order is therefore a highly valued skill, necessary to the physical health of the patient and the financial health of the care provider.

Requiring fast, accurate responses for an ever-expanding list of diagnostic questions, clinical laboratories turn more and more frequently to answers from molecular genetics. This rapidly evolving discipline comprises the study of gene structure and function at the molecular level. The most straightforward diagnostic application of this approach is to search clinical specimens for the presence of a particular gene or a particular allele (one variety of a particular gene). It is possible to use this direct approach to diagnose genetically transmitted diseases such as Huntington's chorea (by detecting the disease-causing allele), or to diagnose occult infections with agents such as *Bartonella henselae,* the agent of cat-scratch disease (by detecting genes specific for that organism). Gene detection tests such as these have already found a welcome place for themselves within the vast arsenal of tests offered by reference laboratories. In some cases (notably the detection of herpes simplex virus in cerebrospinal fluid or *Chlamydia trachomatis* in genital specimens) amplification and detection of genes have become the front-line standard diagnostic tests for conditions difficult to diagnose by other means. These tests require <24 hours from specimen to final result, and replace less sensitive methods with a turnaround time of several days or even weeks. Gene detection tests of this kind remain expensive, however, and have to be tailor-made for one or two organisms at a time. They are not useful for diagnosing disease caused by certain organisms such as bacteria of the genus Staphylococcus, which is normally present on the skin but which can also cause life-threatening disease.

A less obvious application of molecular genetics to clinical diagnosis requires analysis of gene transcription rather than the presence or absence of a particular gene. Disease-associated genes are present in all living things, including human hosts and parasites of all kinds (worms, protozoa, fungi, bacteria and viruses). In some cases, the mere presence of genetic material in a human specimen is enough to signify disease—the presence of genes specific for human immunodeficiency virus, for example, or trisomy 21 for a diagnosis of Down's syndrome. In other cases, however, a "pathological" gene may be present, but clinically silent for a variety of reasons. Examples include the defective hemoglobin gene which causes sickle cell anemia when two copies are present, but minimal disease when one copy is transcribed along with the normal hemoglobin allele, and no disease at all when the sickle cell allele is present but not transcribed. Moreover, genes for certain components of the immune system are present in every cell, but are only transcribed —that is, copied from DNA into RNA—when the host organism is diseased. The presence of these genes is universal, but transcription of them usually indicates a disease state.

In addition to associations between diseases and transcription of particular genes, we find that various combinations of gene transcription are required for specific pathologic outcomes. An example is found in certain lymphomas derived from B lymphocytes. Transcription of the myc gene when the bcl gene is not transcribed in these cells leads to limited proliferation followed by self-destruction of the proliferating cells. If the myc gene is transcribed in the presence of bcl transcription, however, the cell's proliferation is unrestrained, and malignancy may result. The number of two-fold gene interactions is large enough to daunt even the most stout-hearted diagnostic molecular geneticist. When one contemplates the possibility of three-fold, four-fold or more complicated gene interactions, however, it becomes quite impossible to analyze all the possible interactions using methods which detect transcription of only one gene at a time.

Identification of transcription products typically involves five steps: RNA extraction, amplification, hybridization, labeling, and detection, with labeling usually performed during the hybridization or amplification steps. The researcher disrupts the sample in the presence of enzymes which inhibit degradation of RNA. Organic solvents remove protein and lipids, while differential acid and salt concentrations enrich RNA in and deplete DNA from the sample. One can amplify the extracted RNA by reverse transcription (making DNA from an RNA template) followed by the polymerase chain reaction (PCR—which makes a double-stranded DNA product), or by transcription-mediated amplification (TMA—which makes a single-stranded RNA product). At this stage a "label" may be incorporated into the amplified product. Labels are small molecules bound to the components of nucleic acids. Ideally, the label does not interfere with nucleic acid chemistry. The label allows detection in one of four ways. It can emit radiation, it can serve as substrate for an enzyme, which makes a colored product, it can emit light itself (luminescence or fluorescence), or the label can serve as antigen for an antibody bound to a larger molecule which has one of the first three functions. The resulting product, with or without label, is then hybridized to a nucleic acid "probe" of known sequence. In general, either the probe is bound to a fixed surface and the amplified target is labeled, or the amplified target is bound to a fixed surface and the probe is labeled. Following hybridization, the probe produces radiation, light or color reaction. In measuring this, one identifies the presence of nucleic acid complementary to the probe in the target amplified from the original specimen.

To better understand the transcription process, and more specifically hybridization, an individual must understand the roles of nucleic acids in the process. Nucleic acids are chains of subunit molecules called nucleotides, which can be assembled in any order. The length of a chain is denoted by a number followed by the suffix '-mer', hence, dimer, trimer, tetramer, and so on to decamer, with longer chains denoted by "11-mer", '24-mer' etc. DNA is made of the nucleotides deoxyadenosine (A), deoxycytosine (C), deoxyguanosine (G) and deoxythymidine (T) while RNA is made of the nucleotides adenosine (a), cytosine (c), guanosine (g) and uracil (u). Nucleic acid sequences are written as strings of letters—for example ACGT, a DNA tetramer. Nucleic acids "hybridize', or form double-stranded molecules, in a defined pattern. A or a lines up opposite T or u, and C or c line up opposite G or g. Nucleotides which line up opposite each other according to this scheme are called 'complements'. The RNA complement to the above-mentioned DNA sequence ACGT would be ugca, while the DNA complement would be TGCA. Hybridization is most specific—that is, a nucleic acid hybridizes solely to its complement—when the temperature is high, the salt concentration low, and the nucleic acid long, typically $\geq 15$ nucleotides.

Single strands of nucleic acids make stable duplexes by hydrogen bonding with strands of complementary bases. Hybridization is the process of forming these duplexes from complementary single-strands of nucleic acids. Both deoxyribonucleic acids (DNA) and ribonucleic acids (RNA) may be hybridized.

Thus a probe sequence, for example DNA, may be immobilized on a solid surface (the probe surface) and used as a probe for a complementary DNA sequence (the target sequence). In general, the probe surface is exposed to a solution, the solution is removed and the surface is washed, and a DNA-detection method is used to determine if complementary target DNA has hybridized to the probe DNA on the probe surface. Such procedures are routine.

Probes for nucleic acids hold great promise for solving a wide-ranging variety of problems in the field of human medicine, veterinary medicine, and plant husbandry. Also, embodiments of the present invention may be used to detect the presence of organisms in other fields, such as the food, cosmetics and drug industries. A further embodiment of the present device may be utilized as a method of separation (e.g. in the context of a gene discovery or a transcript discovery strategy). Indeed, any living organism with RNA or DNA is potentially the subject of technologies that probe for nucleic acids. Key areas include: clinical diagnosis, for instance diagnosing a disease; transcriptional event discovery, for instance discovering that a certain RNA sequence is expressed in a given biochemical or physiological circumstance; and epidemiological tracking, for instance testing people for the presence and/or type of a virus.

When attempting to solve the wide range of problems described above, it is particularly useful to use a patterning approach. Different probe sequences are immobilized in probe patterns on the surface so that the location and identity of each sequence corresponds to a particular known location, or address, on the probe surface. The group of sequences that is used in the probe pattern is termed an array. Arrays may consist of a complete or a partial set of sequences; a set of sequences is the set of all possible combinations of sequences for a given condition. For instance, an oligonucleotide sequence that is eleven bases long and made of two unique bases, say adenine and cytosine, makes a set of $2^{11}$ or 2,048 sequences; the array could have less than 2,048 sequences; and the probe pattern includes the array and its addresses. A detection means is used to detect the presence and/or quantity of a nucleic acid strand that hybridizes to a sequence in the probe pattern. The detection means are well-known to those familiar in the art and include fluorescent, enzyme-based markers, various staining agents, radioactive, and colorimetric means. A probe sequence is a sequence immobilized to the surface.

The patterning approach is in commercial use and has been described in patents, for instance those assigned to Affymetrix, such as U.S. Pat. Nos. 5,837,832 and 5,770,456.

Thus it is possible, for example, to immobilize oligonucleotide arrays on a chip surface, expose the patterned chip surface to RNA derived from human tissue sample that contains RNA, and examine which addresses on the chip have hybridized with target RNA sequences. Such an approach is thought to be the most useful if the target nucleic acid sequence is known.

Indeed, if current hybridization technology is to be used, it is necessary to know what target DNA or RNA sequence to probe for. A known target sequence is crucial for clinical diagnosis, for transcriptional event discovery, and for epidemiological tracking. To diagnose a disease by hybridization, it would be necessary to discover some sequence that is expressed differently in the diseased patient as compared to a healthy patient or, in the case of an invasive organism such as a bacterium, to know a target sequence specific for the pathogenic strain of that bacterium. In the case of transcriptional event discovery, it is necessary to discover and synthesize a probe sequence for every allele of every gene of interest in order to learn how a certain biological event affects transcription globally. To perform epidemiological studies to detect the presence of a pathogen, for instance, a virus or a bacterium, it is necessary to know the pathogen's sequence and to understand how that sequence may be affected by mutation or normal variation as the pathogen moves through the populace.

But disease specific target sequences are generally not known; current technology is limited to the special circumstances in which a target sequence is already known. In the vast majority of situations the target sequence is unknown because the human genome is only partially sequenced and the activity and function of the known sequences is understood only in a very limited way. Therefore even if every gene were sequenced and every biomolecule made by every gene were known, it would still not be clear what each gene does or how to take advantage of that knowledge.

Further, genes often work together to produce an effect. But assaying for the presence and expression of multiple genes or gene sets is prohibitively difficult. So even if all the human genes were sequenced and their products were known, and the biochemical functions of their products were known, it would generally be impossible to predict exactly which genes to probe for in a given situation. And even if the key genes were known, it is likely that the level of their expression would be important, i.e., if the gene's product is present in a relatively high or low amount. Therefore, current hybridization-based technologies, which are based on the need to know the target sequence, are inadequate for use with conditions requiring knowledge of how genes work together.

And sequencing projects comparable to the Human Genome Project for obtaining genetic libraries for many plants and animals of interest is not even contemplated. Nor are sequences for pathogens commonly known; indeed, the variation and mutation of viruses causes their sequences to be in flux over time.

Thus, the current potential of technologies based on hybridization techniques are limited by the need to know a target sequence. But the present invention solves this need.

SUMMARY OF THE INVENTION

The present invention comprises a non-cognate hybridization system (NCHS). The NCHS generally includes a hybridization technology that is simply and economically used to probe for non-cognate nucleic acid sequences, i.e., for nucleic acid strands without known target sequences.

NCHS causes nucleic acids, bound to a probe surface, to create a hybridization pattern that provides information about the presence and/or quantity of the nucleic acid sequences in a sample. The NCHS results normally orient the examiner towards a small number of specific diagnoses across a wide variety of diagnostic categories (including but not limited to infections, neoplasms and autoimmune diseases). The test will also identify final-common-pathway syndromes such as sepsis, anaphylaxis and tumor necrosis. While the test utilizes genetic information, it does not depend on prior knowledge of the genes involved in a particular disease or syndrome.

The test should be used whenever the following three conditions apply: 1) substantial diagnostic uncertainty; 2) illness severe enough to limit activities of daily living; and 3) possibility of a treatable diagnosis. These criteria usually apply in critical care admissions, as well as many emergency room visits and some chronic disease states. There are approximately 22 million hospital admissions in the United States each year, and it is estimated that at least one in ten such admissions would meet the criteria outlined above. Rounding downward, and discounting the possible use of the test in follow-up or in outpatient settings, it is estimated that hundreds of million of tests per year are indicated in the United States alone. In addition to clinical demand, a smaller demand for use of the system as a hypothesis-generating research tool is anticipated.

Embodiments of the present invention include probes for nucleic acids, which hold great promise for solving a wide-ranging variety of problems in the field of human medicine, veterinary medicine, and plant husbandry. Also, embodiments of the present invention may be used to detect the presence of organisms in other fields, such as the food, cosmetics and drug industries.

The present invention also includes embodiments which can be utilized to detect and identify living and dead organisms. For example the analysis of an environment, such as "water sources" or "sterilized (or clean) rooms" for bacteria. Furthermore, embodiments of the present invention include software, which can be utilized to recognize patterns in addition to hybridization patterns and assess their relatedness to known patterns (e.g. 2D gel electrophoresis patterns).

A further embodiment of the present device may be utilized as a method of separation, differentiation and prognostication (e.g. in the context of a gene discovery or a transcript discovery strategy). Prognostication would include the potential to predict and diagnose genetic and other health related issues in living organisms. In regards to separation, the physical surface of the array can be utilized to identify and specifically analyze the nucleic acids hybridized on relevant addresses. This can be used for gene discovery purposes or transcript expression purposes.

The present invention can be utilized in many other types of applications. Therefore, these and other aspects of the invention will be evident upon reference to the following detailed description.

DESCRIPTION OF THE INVENTION

Figure 1A:
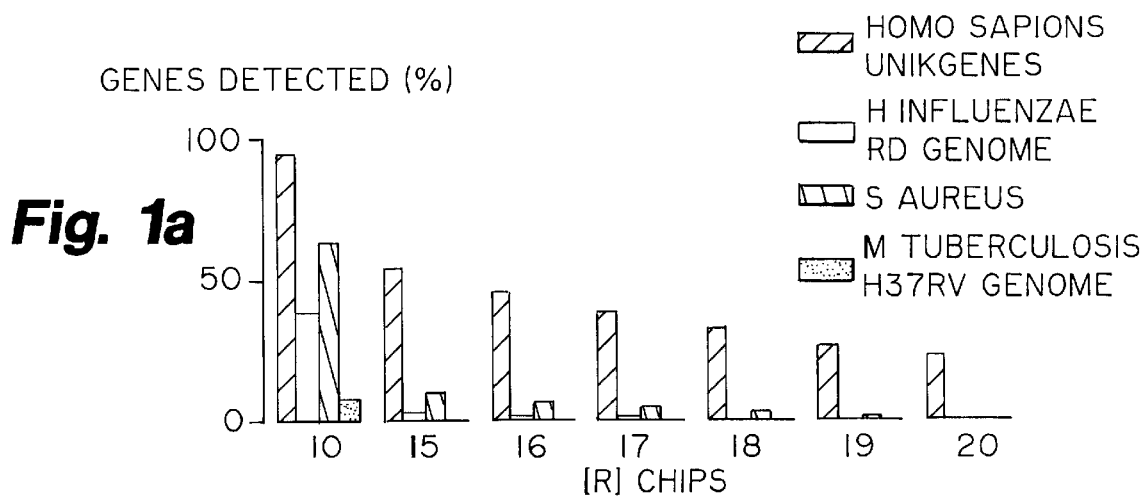
FIG. 1a depicts the results of an R probe surface chip for various species.

The invention is a non-cognate hybridization system (NCHS). This disclosure of NCHS describes how hybridization technology may be simply and economically used to probe for non-cognate nucleic acid sequences, i.e., for nucleic acid strands without known target sequences. The invention causes a sample's nucleic acids to be bound to and distributed on a probe surface in a reproducible and quantifiable manner. NCHS causes the bound nucleic acids to create a hybridization pattern that provides information about the presence and/or quantity of the nucleic acid sequences in the sample. The pattern is created by immobilizing nucleic acid probe sequences to specific addresses; the sequence at each address is known. But it is not necessary to know target sequences to create the probe sequences. Instead, NCHS relies upon a complete set of probes of a known length and composition to identify conditions for which there may be no previously identified target sequence.

Techniques for immobilizing oligomers to specific addresses are commonly known. Typical processes include photolithographic mask-based processes similar to those used for making computer chips. Some of these techniques are patented (e.g., as assigned to Affymetrix and Affymax) or commercially practiced, e.g., by Affymetrix and Incyte. Such techniques may be used to immobilize the oligomers of the invention. Such techniques also encompass means for detecting sequences hybridized to the probe surface; these techniques may also be used with the present invention.

In this invention, nucleic acid probe sequences immobilized to the probe surface may be immobilized as strands of 10 or more hybridizable bases, e.g., bases of RNA, DNA, their synthetic variants, analogues such as PNA (peptide nucleic acids), or molecules with a related chemical design. Herein, a sequence of two or more bases may be referred to as an oligomer and the number of its bases may be specified numerically, i.e., a 12-base oligomer is a 12-mer, a 10-base oligomer is a 10-mer, etc. Preferably oligomers with 10 to 30 bases are made and oligomers in the 13- to 17-base range are especially useful. As previously mentioned, generally probes include but are not limited to DNA, RNA or analogues, such as PNA (peptide nucleic acids). Generally targets include but are not limited to DNA or RNA.

In NCHS, the oligomer probes are immobilized as arrays of all possible sequences generated from a set of two or more unique bases. The probe surfaces are exposed to samples and hybridized with nucleic acids therein. Instructions provided with the probe surface will specify conditions specific to the surface and the assay. The presence and/or amount of nucleic acid hybridized to the various addresses on the probe pattern forms a hybridization pattern that is a profile of the test subject's RNA and/or DNA. This profile hybridization pattern may be compared to reference hybridization pattern (s). This comparison would be the basis for establishing a clinical diagnosis, transcriptional event discovery, epidemiological tracking, or other applications.

The reference hybridization pattern could be generated from samples with the characteristics that are being probed for. So if a disease is being probed for, hybridization pattern(s) generated from subject(s) with the disease could be used as references. For example, 10 samples taken from each of five rabid dogs for a total of 50 references could be used to establish a single reference or a group of reference patterns that show a range of hybridization patterns for a rabid dog. Another series of samples taken from healthy dogs could be used as a second reference or healthy standard. If hybridization patterns from a subject dog fit within the hybridization pattern parameters established for a subject dog, then the rabid dog would be diagnosed with rabies.

This example points to a significant advantage of NCHS: it provides for an open-ended assay. Other currently used and known assays are close-ended: the assay can probe for only a predetermined set of sequences. For example, to diagnose rabies using a predeterminate hybridization strategy would require knowledge of how rabies affects gene expression and would be based on a probe that targeted known sequences. Further, the test results would capture information about the presence and/or quantity of the target sequences present.

In contrast, the NCHS open-ended strategy for rabies diagnosis would merely compare the hybridization pattern of expressed genes between a healthy subject and one suffering from rabies. It would not be necessary to know what nucleic acids constituted a target sequence. Further, the NCHS strategy enables simultaneous assay for multiple conditions. Thus a subject's hybridization pattern could conceivably be used to simultaneously diagnose a dog for heartworm, rabies, distemper, parvovirus, adenovirus, adenocarcinoma and Lyme's disease using a single assay.

Indeed, the invention contemplates a database that would retain the hybridization patterns of subjects. Thus an open-ended epidemiological study for HIV that captured a profile hybridization pattern of RNA and/or DNA for every person in the study could later be examined for information about the expression of a pattern of sequences linked to incidence of cancer. Thus, the NCHS database would contain inherently open-ended assays that would answer specific questions and also provide information that could be later interpreted in light of a different question.

Regarding embodiments of the present invention, the probe pattern may be formed from one or more arrays. The lengths of oligomers may be held constant or varied within an array or from array to array. For example, a 15-mer made from adenine and guanine would form a set of $2^{15}$ or 32,768 combinations that could be immobilized as one array on a probe surface.

Figure 1B:
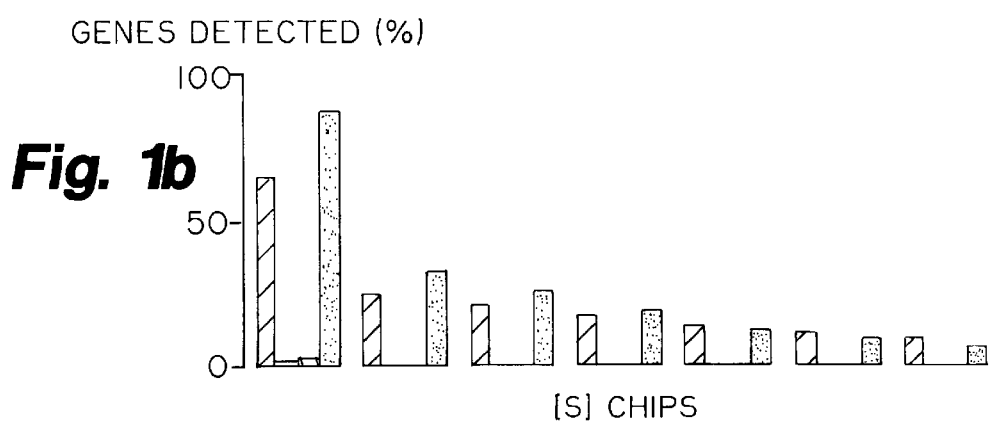
FIG. 1b depicts the results for an S probe surface chip for various species.
Figure 1C:
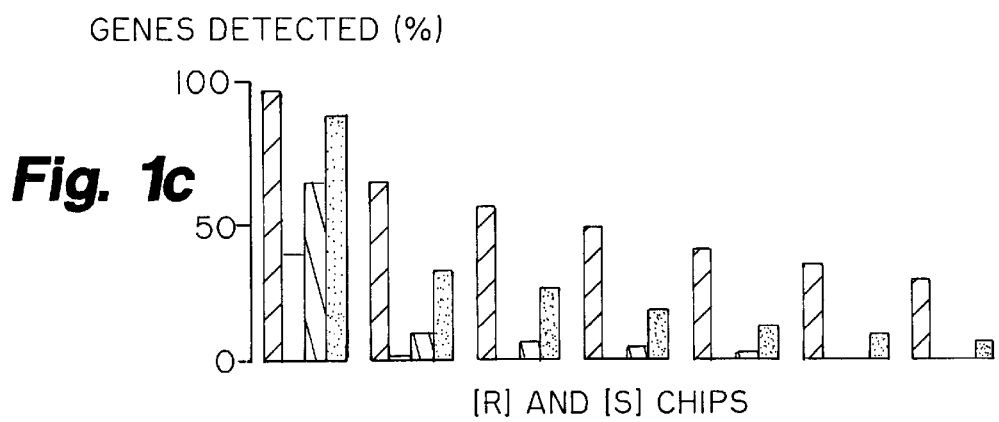
FIG. 1c shows the combined results for R and S probe surface chips for various species.

FIGS. 1a, 1b, and 1c show the unexpected results obtained by using oligomers consisting of two unique bases that range in length from 10 to 20 bases. In this experiment, arrays of all possible combinations of oligomers made with two unique bases and a fixed length ranging from 10 to 20 bases were tested for binding of genes from humans and microorganisms. First, arrays of random DNA sequence were generated that were equivalent to the sets of all the possible combinations of either adenine and guanine or guanine and cytosine for sequences with lengths of 10, 15, 16, 17, 18, 19, or 20 bases. It is noted that in all the figures (R) represents adenine and guanine and (S) represents guanine and cytosine. Then, four different genome databases (*Homo sapiens* UniGene, *H Influenzae* Rd genome, *S. aureus*, *M tuberculosis* H37Rv genome) were compared to the arrays to determine what percentage of the genes in the database would bind to an address in the array. Although only two unique bases were used and even though the sequences were randomly generated, the arrays could hybridize significant fractions of the genome. For instance, in FIG. 1a, 10-mers of adenine and guanine were hybridizable with more than 90 percent of the expressible human genome sample. And 15-mers bound more than 50 percent, while 20-mers bound more than 20 percent.

Furthermore, FIGS. 1a–1c show that sensitivity for *Homo sapiens* declines approximately 25–50 percent for each five-base increment in length for the AG and GC oligonucleotide subsets. Similar inverse relationships were observed between size and sensitivity for each two-base oligonucleotide subset (data not shown). The figures also show that the AG and GC oligonucleotide subsets are almost entirely additive to each other with respect to sensitivity. In fact, this pair offered the highest sensitivity of any combination of two oligonucleotide subsets, and the addition of other subsets offered only modest improvements. When all six subsets were combined, they detected 78–85 percent of human genes, 53–64 percent of *Staphylococcus aureus* genes, 16–24 percent of *Haemophilus influenzae* genes, and 28–36 percent of *Mycobacterium tuberculosis* genes, for 16 and 15 oligonucleotide subsets, respectively.

These results show that a simple array of random sequences hybridizes with a large fraction of the genome of a living organism. Therefore the hybridization pattern of the genome on a probe pattern made from such array will create a distinctive profile. In contrast, to create such a pattern with a close-ended technique would require hundreds or thousands of specifically designed sequences, carefully selected from known and understood sequences.

The economical cost and simplicity of creating sequences based on only two unique bases is striking. In the first place, there is no prior research necessary to discover what probes to bind to the solid surface. Also, the synthesis of the probes on the solid surface is simplified by using less than four unique bases because steps for coupling the other two unique bases are eliminated and because fewer, simpler masks may be employed. Since arrays of similar sequences are used, the probe pattern may be designed to simplify the synthesis and masking steps. In contrast, a large array of probes designed for known target sequences will typically not have similarities in sequences that may be used to simplify the manufacturing process.

As previously mentioned, FIGS. 1a, 1b, and 1c depict how the percentage of the genome that is bound by complete sets of combinations of two unique bases decreases as length of the oligomer increases. This trend occurs because increases in the length of a random sequence decrease the possibility that the random sequence will find a complementary sequence in a gene. Furthermore, the choice of unique base pairs also affects hybridization because some genomes are particularly rich in certain bases. For instance the human genome is rich in adenine and thymidine so that adenine-containing combinations bind more of the human genome than other combinations (FIGS. 1a–1c and 2a). And *M tuberculosis* is particularly rich in guanine and cytosine so that this combination of bases binds more *M tuberculosis* than other combinations (FIGS. 1a–1c and 2a). It is noted that in FIGS. 2a–2b and 3a–3b the genome is indicated by the legend: bottom position (black) is *Homo sapiens,* second position (dark grey) is *H influenzae;* third position (light grey) is *S aureus;* and top position (white) is *M tuberculosis.* Also, regarding FIGS. 1a–1c, 2a–2b and 3a–3b, the letter definitions are as follows: A=deoxyadenosine (adenine), C=deoxycytosine (cytosine), G=deoxyguanosine (guanine), T=deoxythymidine (thymidine), K=G and T, M=A and C, R=A and G, S=C and G, W=A and T, Y=C and T, H=A, C and T, B=C, G and T, V=A, C and G, and D=A, G and T.

Figure 2A:
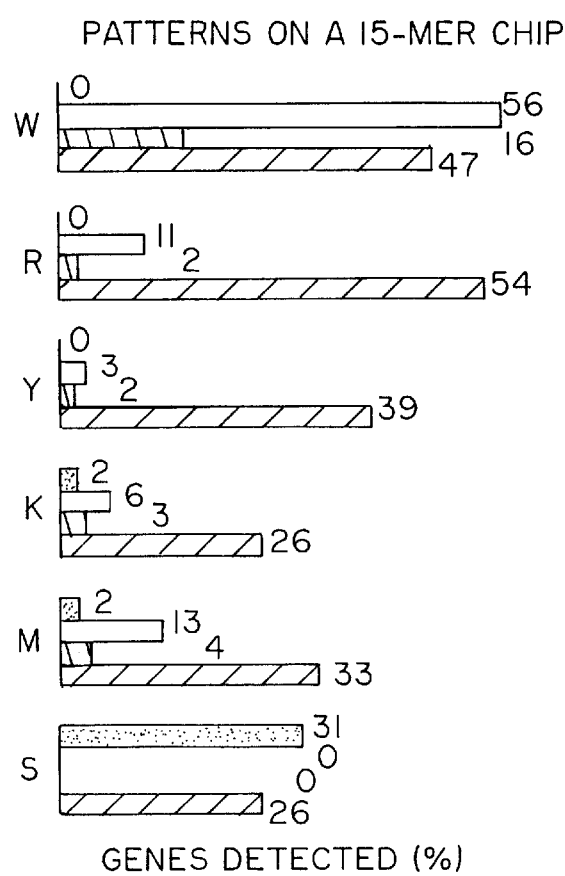
FIG. 2a depicts the percentage of genes captured on a 15-mer chip that would be bound for various species.
Figure 2B:
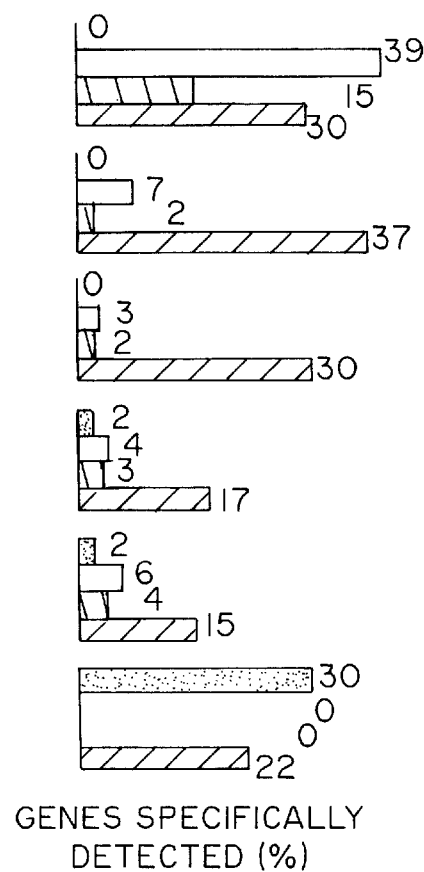
FIG. 2b shows the percentage of genes captured on a 15-mer chip that would be the only gene to bind to a particular sequence of the array for various species.
Figure 3A:
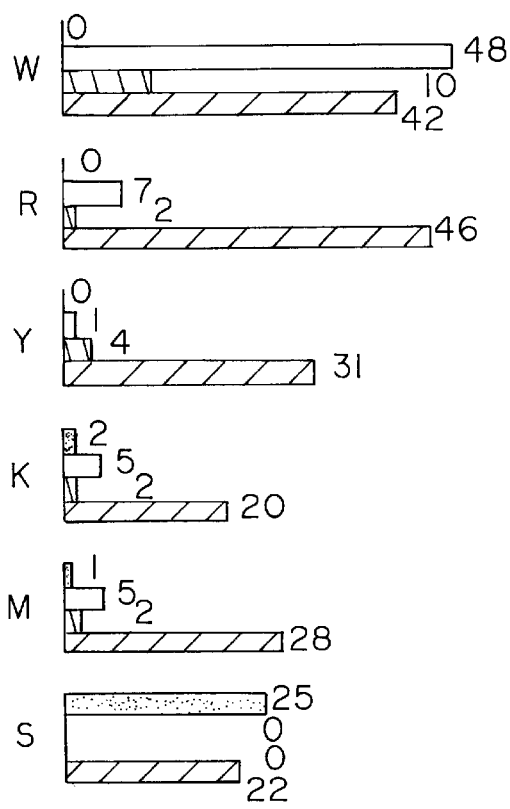
FIG. 3a shows the percentage of genes captured on a 16-mer chip that would be bound for various species.
Figure 3B:
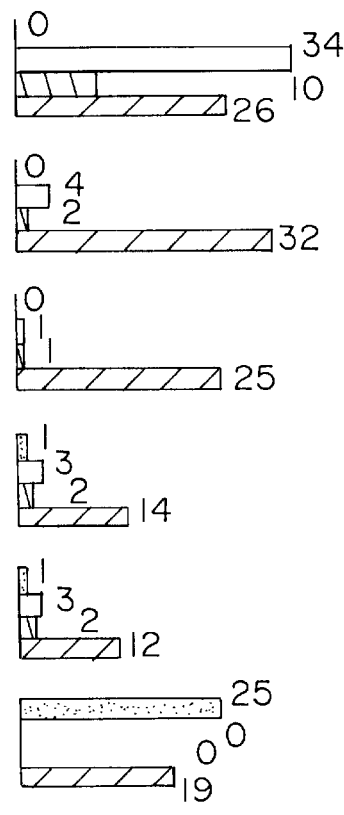
FIG. 3b shows the percentage of genes captured on a 16-mer chip that would be the only gene to bind to a particular sequence of the array for various species.

Another unexpected phenomenon was observed when arrays based on two-base combinations were tested against genomes. Not only was a large fraction of an organism's genome hybridizable, but a large fraction of it was hybridizable to a unique address; in other words, some genes would hybridize only to one sequence in the array. Therefore detection of nucleic acid sequences at that address would indicate the presence and/or quantity of that unique gene. FIG. 2b shows that an array of 15-mers of adenine and guanine (R) will hybridize 54 percent of the human genome: remarkably, the combination of only these two bases will hybridize 37 percent of the (currently known) human genome to distinct addresses on a probe surface. A 16-mer (R) array will bind 32 percent of the human genome uniquely, indicating that the simpler, shorter 15-mer actually uniquely identifies more genes than the 16-mer. Similarly, guanine and cytosine combinations of 15-mers uniquely identify 30 percent of the *M tuberculosis* genome and 16-mers bind specifically 25 percent of the same genome. See FIGS. 2a–2b and 3a–3b.

Also sensitivity correlated with the percentage of specific matches, but both varied markedly between oligonucleotide subsets. FIG. 2b shows that the AG subset (R) offered the highest sensitivity and the highest percentage of specific matches within the human gene database, while the AT subset (W) offered the highest sensitivity and specificity for *Haemophilus influenzae* and *Staphylococcus aureus*. *Mycobacterium tuberculosis* was the only GC-rich organism included in the study, and only the GC subset offered substantial sensitivity for this organism. For each oligonucleotide subset and for each gene database, >65 percent of all genes matched had one or more gene-specific oligonucleotide matches.

This high percentage of specific matches was conserved when genomes from two organisms were mixed and tested against the same oligonucleotide subset. When the 15-nucleotide AG subset, for example, was tested against a mixture of *Homo sapiens* and *Staphylococcus aureus* genes, 66 (83 percent) of 80 specific matches with the *Staphylococcus aureus* gene database remained specific, and 4,550 (99.7 percent) of 4,564 specific matches with the *Homo sapiens* gene database remained specific. Similarly, when the 15-nucleotide GC subset was tested against a mixture of *Homo sapiens* and *Mycobacterium tuberculosis* genes, 4,532 (85 percent) of 5,351 matches remained specific in the mycobacterial genome and 3,179 (80 percent) of 3,998 matches remained specific in the human gene database.

These results show that the sequence length and choice of bases may be manipulated to increase or decrease the amount and specificity of binding. This manipulation can be used to control hybridization patterns. This control ensures that useful profiles may be created in a wide variety of circumstances. It may be desirable, for instance, to have a group of three arrays that create different hybridization patterns from the same sample: a first member of the group could capture a large fraction of the genome; a second could be designed to capture a maximal number of genes uniquely, and the third member could be designed with characteristics in between the other two. Or, an assay directed toward a specialized tissue might be designed to emphasize unique localization for a high-resolution snapshot of gene function or presence. Or, a screening assay might be directed to maximal capture of RNAs.

The addresses that capture a gene uniquely may lead directly to the discovery of gene functions and expressions. They may also be especially helpful markers in patterns. For instance, an address that hybridizes to three genes or gene fragments would not necessarily reflect changes in the relative concentrations of each gene, but an address unique to one gene or gene fragment would reflect such changes. Or, for example, hybridization patterns from persons suffering from multiple sclerosis could be compared to reference patterns and the nucleic acid sequences that increased or decreased in the diseased patient could be pulled off the probe chip and sequenced. These sequences would point to genes and/or gene products involved in the disease.

As previously mentioned in the background of the invention, the identification of transcription products typically involves five steps: RNA extraction, amplification, hybridization, labeling and detection, with labeling usually performed during the hybridization or amplification steps. Methods for these steps have all improved to the point where very small amounts of template material—as few as one to ten molecules in a sample—can be identified within 24 hours. In most diagnostic assays, however, these methods have significant drawbacks. Because of their sensitivity, amplification methods are highly susceptible to false positive results, due to as few as one errant molecule which wandered into the reaction mix. Both the amplification and hybridization steps can require hybridization to a specific complement, thereby increasing specificity somewhat. Because of this specificity, however, conventional molecular diagnostic tests rely on knowledge of one's target molecule, and are designed for one organism at a time.

One way of circumventing the one-at-a-time limits of molecular testing is to use a "broad-range" approach to amplification. In this approach, one attempts to amplify all target sequences, or at least a broad cross-section of them. The resulting products then have the opportunity to hybridize to a large number of probes simultaneously, and detection of the probes which actually hybridize reveals the presence of the gene(s) of interest. When multiple probes are used in this fashion, they are almost always bound to a solid surface while the labeled, amplified template is exposed to the probes in solution. Unbound amplified template (and label) are then washed away, and only the probes which hybridized are visible in the detection step.

For this sort of assay, nucleic acid probes can be bound to a variety of surfaces, including nitrocellulose, nylon, glass and silicon. Most recently, research has emphasized automated methods whereby precisely defined nucleic acid sequences (probes) can be deposited or even directly synthesized on minutely defined locations of a glass or silicon surface. These resulting glass slides or silicon chips then hybridize to a solution of labeled amplified template. A microscopic image of the slide or chip reveals the presence or absence of label in each probe-specific locus. In this way, one discovers which of many possible probes are represented in the original template. It is possible to load a million different probes onto specific loci of a single chip, using photolithography procedures practiced by Affymetrix, Inc. Thousands of probe-specific loci can be created on a glass slide using procedures that are in the public domain. Assays based on these methods are used to detect drug resistance-associated mutations of the human immunodeficiency virus (HIV) genome, and other applications are following rapidly. The HIV chip, as well as other methods, rely upon prior knowledge of specific sequences in order to provide information about an unknown patient sample.

An embodiment of the present invention is a robust strategy for chip- or slide-based molecular diagnosis. It shares with its predecessors the speed, accuracy and sensitivity typical of molecular assays. Unlike the diagnostic chips known to be under development, however—and even more distant from their one-gene-at-a-time antecedents—the invention requires no prior knowledge of target genes. It analyzes expression of multiple genes simultaneously, and is less likely to be invalidated by a single constant. Moreover, the new invention allows detection of an essentially infinite variety of diseases, syndromes and variants of normal on a set of finite platforms. Use of these platforms will allow development of an expanding database which can be programmed to improve its diagnostic accuracy with each accrual of new information, and could be used as a first and sometimes final test leading to accurate diagnosis of literally thousands of conditions. In addition, the invention is likely to find extensive use as a tool for hypothesis generation and gene discovery.

The procedure of this embodiment begins with reverse transcription of an RNA template extracted from clinical specimens (usually erythrocyte-depleted blood). This results in complementary DNA -(cDNA) which then serves as template for a nonspecific, random hexamer-driven amplification procedure (TMA or PCR). If TMA, fluorescent label is incorporated directly into the product. If PCR, label is incorporated into a transcript of the product. The product of amplification is fragmented (e.g., by heat in the presence of magnesium) and the products (average length 30 to 50 bases) are exposed to the diagnostic chip for hybridization, under conditions specific for that chip.

The diagnostic-chips comprise an array of nucleotide multimers. Computational genomic analysis suggests that a specific set of chips (see below) are likely to provide the greatest information at the least cost but the present invention is not limited to this specific set of chips and the concept of the present invention incorporates collections of multimers from 10 to 30 nucleotides in length that may be utilized with any probe or chip surface.

In an embodiment each chip comprises all possible X-fold combinations of N nucleotides, where N=2, 3 or 4 and X is the length of the nucleotide sequence. As hybridization reactions have limited specificity when X<15, we propose that when X<15, X will represent one end of a longer oligonucleotide X+Y, where Y=(15−x), Y comprises a random mix of all possible Y-mers, and Y is attached to the surface of the hybridization chip. Each Xmer will have its own physical domain. The chip also incorporates standardization domains for detection of a first external control with which the sample is "doped" prior to extraction, a second external control with which the sample is doped after extraction and prior to amplification, a third external control with which the sample is doped is after amplification and prior to detection, and internal controls comprising genes constitutively expressed at levels which are relatively constant per living cell regardless of external conditions.

Another embodiment may include a chip with multiple X-fold combinations. Therefore it may be possible to utilize and analyze a single chip with multiple values for X. This could provide, for example, a single chip with a 15-mer and 16-mer set of oligonucleotide combinations.

Detection of label in a domain-specific fashion (using a confocal microscope, scanner or other micro-imaging technology) allows detection of complements to each probe represented by each domain. Existing technology allows grading of signal intensity over about a 100-fold range, with 100 levels of discrimination between the highest quantifiable and lowest detectable signal. Results are analyzed in samples from patients with known diagnoses from a medical center of clinical excellence. Nonlinear statistical methods, including neural networking algorithms and indexing algorithms under development, identify patterns in the data associated with specific diagnoses. The identified patterns are then tested in a validation dataset of new patients from the originating medical centers as well as others. In this way, new diagnoses will be added to the available database in an ongoing fashion.

Preliminary analyses of this method have been performed using databases derived from GenBank and the European Molecular Biology Laboratory (EMBL). In brief, it is assumed, from published data, that approximately 10 percent of the genes in a eukaryotic organism are transcribed in any given tissue at any one time, and a clinical event (e.g., genetic disorder, syndrome, disease, injury or intoxication) will have direct influence upon transcription of approximately 10 percent of the genome (some of which include constitutively expressed genes). There are six possible chips where N=2, AT, AG, CT, GT, AC and CG. Among these, note that the single most sensitive chip (AG) can detect >50 percent of the genes represented in a database of 2,736 human genes (with multiple alleles excluded); almost 40 percent of genes hybridize with probes that detect only one gene and no other gene. No detection system, on line, in prototype or in development, is capable of sampling even one percent of the human genome on a single assay. The AG-15 chip will also detect >10 percent of genes in a database comprising 468 *Staphylococcus aureus* genes from GenBank and EMBL. A similar analyses has been performed for each N=2 chip from X=15 to X=20, alone and in combinations of two chips, against *Homo sapiens* genes, *Staphylococcus aureus* genes, *Haemophilus influenzae* genes and *Mycobacterium tuberculosis* genes. The results show that even one or two chips in the X=15 series will detect most events which perturb expression of human genes, while the complete set of six chips will allow semiquantitative detection of almost every human gene in the existing databases. Note that each X=15 "chip" is an array of approximately 32,000 domains, and that all six arrays would fit on one of the prototype million-domain Affymetrix chips with ample room for control domains and redundancy.

Another embodiment of the present invention also describes how biological patterns can be recognized by open-ended analysis of broadly defined oligonucleotide subsets. The amplification and identification of genes or gene products have become mainstays of biomedical research in general and laboratory diagnosis in particular. It is sometimes possible to identify specific associations between particular sequences and particular diseases. There are significant limitations to this one-disease-at-a-time strategy, however. Identification of informative target sequences requires vast prior investigations, sequencing is often required to confirm or exclude diagnoses, many assays may be required when the diagnosis (and therefore the correct test) is not obvious, and the overall approach is very costly. Hence there is demand for multi-target gene expression assays, and massively parallel strategies for their analysis.

Hybridization technology now allows nucleic acid amplification products to be compared with thousands of sequences simultaneously. Intense interest in this approach has resulted in commercial development of multigene arrays, which may be used to look for disease-specific profiles on the basis of expression of known genes. These arrays remain dependent on prior research defining the genes of interest. Most are targeted to the normal human genome, offering limited opportunity to learn either from unusual alleles, not to mention from unknown genes or from the genome of pathogens.

These are intrinsic limitations of closed-ended strategies requiring prior understanding of established sequences. It is not necessary, however, to rely upon patterns we understand. There is ample precedent for discovery of diagnostic, preventive and even therapeutic modalities long before a mechanism is understood. Rather than a limited collection of known genes, the invention proposes open-ended analysis of a broadly defined set of oligonucleotides hybridized with amplification products from the target material.

Biochemical considerations presently limit sequence-specific hybridization reactions to oligonucleotides of 15 bases or greater. For this study, the use of 15-, 16-, 17-, 18-, 19- and 20-base oligonucleotides as well as decamers was analyzed. The diversity of an oligonucleotide subset of length n is $X^n$, where X is the number of bases represented in the set. The diversity of a complete set of nucleotides is $4^n$, or $>10^9$ for a set of 15-base oligonucleotides. This is too many to fit on an analyzable surface at present. Therefore, oligonucleotide subsets composed of the six possible pairs of bases were analyzed, and each oligonucleotide subset was tested against genomic databases for sensitivity and for specific matches. For this analysis, sensitivity was defined as the percentage of genes in a database which had an exact match with at least one oligonucleotide in a subset. Specific matches were defined as exact matches between a gene and an oligonucleotide, when the oligonucleotide did not match any other gene in the database.

Another embodiment of the present invention also includes the utilization and analysis of portions of the previously mentioned oligonucleotide subsets. If an oligonucleotide subset is $X^n$, as shown in the previous paragraph, a portion of that oligonucleotide subset of bases is $<X^n$. For example if X=2 bases and n=15 there would exist 32,768 possible combinations of bases. Therefore, this embodiment of the present invention includes the utilization and analysis of an array comprising a percentage of less than 100% of the possible 32,768 combinations of bases.

Another embodiment of the present invention may include a chip with multiple X-fold combinations, using different subsets or portions thereof. This could provide for example, a single chip with a (S)15-mer and portion of a (R) 16-mer set of oligonucleotide combinations.

Examples of complete databases which can be utilized in the present invention are as follows:

1) 1,709 *Haemophilus influenzae* genes (on the world-wide web at tigr.org/tdb/mdb/hidb/hidb.html);
2) 3,918 *Mycobacterium tuberculosis* genes (on the world-wide web at sanger.ac.uk/Projects/M tuberculosis/blast server.shtml);

Examples of partial databases utilized in the present invention are as follows:

1) *Staphylococcus aureus* genes (Look-up function in GenBank, for *Staphylococcus aureus* in the organism field); and
2) *Homo sapiens* genes (on the world-wide web at ncbi.nlm.nih.gov/UniGene/Hs.Home.html). From these databases, complete cDNA sequences or genes are selected, without apparent redundancy and without multiple alleles of the same gene, yielding 468 and 2,736 genes, for *S. aureus* and *Homo sapiens*, respectively.

Matching is analyzed in three stages. First, each database is interrogated with the Wisconsin package (Wisconsin Package Version 9. 1, Genetics Computer Group (GCG), Madison, Wis.). "Findpatterns" is used to seek oligonucleotides of a given length and base composition (AT, AC, AG, CT, CG or GT) on one strand of the sequences. Only exact matches were kept for further analysis. Monarch (Version 4.02, Datawatch Corp, Wilmington, Mass.) is utilized to parse the output from each "Findpatterns" command to produce a spreadsheet with one line for each oligonucleotide-database match, including fields for the oligonucleotide sequence, the gene matched by the oligonucleotide, and the site on the gene where the match occurred. Finally, Origin (Version 5.0, MicroCal Software Inc., Northampton, Mass.) and Excel (97-SR I, Microsoft, Redmond, Wash.) are utilized to sort the matches, enabling a count of the number of genes matched by each oligonucleotide and the number of oligonucleotides matched by each gene.

Another embodiment of this invention is a series of arrays generated by the techniques described herein that uniquely or even redundantly capture an entire genome or set of genomes. The approach described herein succinctly sets forth the concepts necessary to enable the creation of the probe patterns by those skilled in the art. First, a group of arrays may be generated by making complete sets of combinations of nucleic acid bases. Then the group may be tested against a genome library to determine which combination of sets uniquely bind each gene in the library. Then, sequences that do not bind any genes may be eliminated. Since a 15-mer of adenine and guanine will specifically bind 37 percent of the (currently sequenced) human genome with only 32,768 combinations, the size of the resulting arrays will be within current manufacturing technology (roughly three million sequences may currently be immobilized on a conveniently-sized probe pattern). The limited number of bases and the random nature of the sequence design will ease manufacturing requirements.

This invention encompasses a new device and methods for performing the applications that are currently performed by gel electrophoresis and related analytical and separations techniques. Such techniques separate nucleic acid strands by physical characteristics such as size, molecular weight, isoelectric point, etc. This invention is similarly capable of performing a separation of mixtures of nucleic acids.

The probe surface may also carry sets of controls. For instance, a few addresses could contain sequences targeted specifically to known sequences. These addresses could be used to set a standard for the detection means. For instance, an address that bound a gene that is present in an amount that is constant from one individual to another could be used to normalize the fluorescence, radioactivity, etc., measured at the other addresses.

Washing or annealing protocols may be used to enhance the type and quality of information recovered from the hybridization patterns. It is commonly known that sequences hybridize with varying strengths of binding. So hybridization patterns may be obtained under a first set of conditions that include a weak washing step. Then the probe surface may be washed again using a stronger washing step that removes more strongly bound sequences with the result that the hybridization pattern is altered. The surface may be put through a series of increasingly strong washes so that not only may the position and presence and/or amount of sequences be detected, but also their affinity for their address. Washing steps may use a variety of solvents, time, temperature, detergents, or other factors, including factors known to affect annealing of nucleic acid strands.

The invention encompasses a database. The database will contain hybridization patterns generated in a wide variety of circumstances. The database includes the hybridization pattern and information about the sample, including time, date, organism, and other circumstances. The database itself will be a valuable resource for correlating or establishing causal connections between the sample hybridization patterns and the database or reference hybridization patterns. For instance, an epidemiological study of seasonal influenza might capture transcription profiles of a large number of infected persons. After entry into this, the database study could later be compared to subsequent years' influenza studies to understand the spread of the virus, of its subtypes, or of mutations.

The database will be useful in a tremendous range of applications. For instance, the database could be part of a query by a scientist seeking proof that leukemia became more common in a given region after a certain chemical was discovered leaking from a storage tank into the local water supply. Just as the human genome database is a vital resource for all types of scientists and sectors of society, so too the NCHS database will provide information about the distribution and expression of the human genome—and other genomes. In another example, hybridization patterns from a series of routine kidney biopsies for the diagnosis of nephronophthisis might be useful to another person studying epidemiological studies or transcriptional events of nephronophthisis.

Another embodiment of this invention is a defined Pan-array. The Pan-array is a diagnostic test that may be performed on nucleic acids extracted from a subject's blood. The test will address a wide variety of diagnostic categories, including infections, neoplasms, and autoimmune diseases, and will indicate a specific diagnosis or a limited number of possible diagnoses. The test will also identify final-common-pathway syndrome, such as sepsis, anaphylaxis, and tumor necrosis. As with the other applications, the diagnostic test does not depend on prior knowledge of the genes involved in a particular disease or syndrome. There is a need for accurate, reliable, and informative diagnostic tests. Indeed, over hundreds of million of diagnostic tests are performed each year in the United States alone, most of which have the possibility of diagnosing only a handful of diseases.

The Pan-Array particular diagnostic test could be used when the following three factors apply: (1) substantial diagnostic uncertainty; (2) illness severe enough to limit activities of daily living; and (3) possibility of a treatable diagnosis. These criteria typically apply in critical care admissions, as well as in many emergency room visits, and some chronic disease states. Of the 22 million hospital admissions in the United States each year, approximately one in 10 such admissions should meet the factors set forth above. Further, these tests should also be useful as a hypothesis-generating research tool. This and other embodiments of the present invention will generate diagnoses based on semi-quantitative information on the expression of approximately 20 percent of the human genome and 50 percent of prokaryote genomes. The previously mentioned percentages have been validated and are based on computational experiments using computer hardware known in the art and software developed for this type of application.

The Pan-arrays will enable multiple diagnoses to be rapidly performed with one assay. Many currently used diagnostic tests require days to complete, are invasive, or are even dangerous to perform, and all contribute to the upward spiral of medical costs. The efficiency, speed, and low cost of Pan-arrays, therefore, will provide an important improvement over current technology.

The blood sample will typically be depleted of erythrocytes. An RNA template will be extracted from the sample and cDNA will be generated by reverse transcription. The cDNA will serve as a template for a non-specific, random hexamer-driven amplification procedure (e.g., TMA or PCR). The amplification product is fragmented (e.g., by heat, the presence of magnesium) and the products (average length 30 to 50 nucleotides) are exposed to the Pan-array's probe surface for hybridization. Instructions provided with the probe surface will specify conditions specific to the surface and the assay.

The probe surface will incorporate standardization domains for detection of a first external control with which the sample is "doped" prior to extraction, a second external control with which the sample is doped after extraction and prior to amplification, a third external control with which the sample is doped after amplification and prior to detection, and internal controls comprising genes constitutively expressed at levels which are relatively constant from individual to individual, or per-living-cell, regardless of external conditions.

Instructions provided with the assay will indicate how to detect the complementary sequences hybridized from the sample to the probe surface; a confocal microscope, scanner, or other micro-imaging technology may be used. Current technology allows grading of signal intensity over approximately a 100-fold range with 100 levels of discrimination between the highest quantifiable signal and the lowest detectable signal.

Software for interpreting the resultant hybridization patterns will be accessible to the medical practitioner. This software and access to the hybridization pattern database will be used to identify patterns in the hybridization data that are associated with specific diagnoses. The software may use currently-known techniques of computation, including non-linear statistical methods and neural-net algorithms. Further, indexing algorithms currently under development may be used.

The present invention also includes a unique software for performing functions such as but not limited to inputting, analyzing, computing, outputting and storing various types of data. The purpose of one embodiment of the software utilized in the present invention is to index a multi-variable data set by groups of three variables, and use the resulting indices to identify variables, which may be associated with a categorical outcome.

Embodiments of the software, referred to as "Index3", has many differences from existing software. The software utilized in embodiments of the present application is dissimilar to completely "open" clustering algorithms such as those used to generate self-organizing maps, in that the outcome variable (dependent variable) is defined. This software is dissimilar to controlled or closed analytical approaches such as Cox proportional hazards or logistic regression in that the input variables (independent variables) are permuted to make a complete set of possible 3-fold indices. The user does not specify in advance which variables are to be combined in a predetermined model. Hence the associations identified by the program need stringent validation.

The input file utilized in embodiments of the present software is a comma-delimited text file (.CSV format) called "input.csv" in the root directory (c: drive). Each column represents a field (or variable, or gene) and each row represents a record (or experiment). The outcome variable, an integer, is in the first column. The field names are in the first row.

Each column represents one field. The field name (as text) is read from the first row of each column. The first row of each column is ignored for analytical purposes. There is no theoretical limit on the number of fields permitted. If the input file is prepared in most spreadsheets, however, there is a limit of 256 columns, including the outcome variable.

Each row (except the first row) represents one record. Each record should correspond to an experiment or set of observations. Qbasic will not accept arrays of >64,000 loci, hence as long as the program remains in Qbasic no more than 21,333 records can be analyzed in a single dataset.

The outcome variable should be in the first column. At present the program is constructed to analyze only binary outcomes, 1 or 2. This is easy to change, but the statistical power of diagnosis declines with the number of possible outcomes.

The data may contain floating-point numbers of any size, however, the program in its current form assumes that numbers within each field have been transformed to a z score (the number of sample standard deviations removed from the mean for all the observations in that variable). At present there is no identification of missing data, which are simply interpreted as zero.

The program reads the entire dataset, and permutes the data fields by groups of three (var1, var2 and var3). Each record in the last third of the dataset is evaluated concerning whether each of the three variables in the current permutation is greater or less than its specified cutpoint (ctpt1, ctpt2, and ctpt3 for var1, var2 and var3 respectively). The cutpoints are also permuted such that ctpt1 includes −1.5, −1, −0.5, 0, 0.5, 1 and 1.5, while ctpt2 and ctpt3 include these values as well as −10. The purpose of the −10 cutpoint is to evaluate univariate and bivariate permutations utilizing var1, since essentially all records should have field values with a z-score>−10. (The cutpoints can be altered by changing the "step" command in the "for" statement referring to ctpt1, ctpt2 and ctpt3). The program sets up 8 tables for statistical evaluation of each permutation of cutpoints for the last third of records in the dataset. These tables are established in an array called stat. In the first table (r=1) a risk of 1 corresponds to var1<ctpt1, var2<ctpt2, and var3<ctpt3. In the second table, (r=2), a risk of 1 corresponds to var1<ctpt1, var2<ctpt2, and var3≧ctpt3, and so on through r=8. Within each table, records are counted in four categories, risk=1, outcome=1; risk=1, outcome=2; risk=2, outcome=1; risk=2, outcome=2. Sensitivity, specificity, positive predictive value, negative predictive value, risk ratio and chi-square (uncorrected) are calculated for each table. When chi-square is less than 4, the program evaluates a new table within stat or (if r=8 and all the tables within stat have been evaluated) proceeds to the next permutation of cutpoints. When chi-square is greater than 4, the middle third of records in the dataset are evaluated with respect to the particular permutation of var1, var2, var3, ctpt1, ctpt2, ctpt3 and r represented by the statistically significant result. If the middle third of records also yields a chi-square>4 for this permutation, the first third of records is in turn evaluated, and the statistical measurement captured in a file called "output.csv" in the root directory (c: drive). While running, the program displays ctpt1, var1, var2, var3, the number of permutations with significant results in one third of the data, the number of permutations with significant results on two thirds of the data, and the number of permutations with significant results on all thirds of the data.

The output file is a comma-delimited file (.CSV format) in the root directory of the c: drive. The program presently does not create field headers for this file, since it is anticipated the user will add evaluations to an existing file. If data are directed toward a new output file, it is useful to preserve the text headers from the output file included with this package. The first nine fields describe the risk criteria used to establish a successful association with the output variable in the last third of records. The next four fields refer to the data cells for this association (a: risk=1, outcome=1; b: risk=1, outcome=2; c: risk=2, outcome=1; d: risk=2, outcome=2). The next six fields contain statistical measures of this association (relative risk, positive predictive value, negative predictive value, sensitivity, specificity, and chi-square, in that order). Thus far, we have reviewed 9+4+6=19 fields. The next 10 field contain the same statistical summary for the middle third of records, that is cells a, b, c and d of a standard 2×2 risk/outcome table, followed by relative risk, positive predictive value, negative predictive value, sensitivity, specificity, and chi-square, in that order. The last 10 fields contain these same statistical data for the first third of records. A set of risk criteria will appear in the output file whenever the last and middle third of records show an association with a chi-square greater than 4 and a consistent relative risk. (That is, the relative risk has to be >1 for both the last and middle thirds, or <1 for both the last and middle thirds). Final validation of the criteria is left to the user, by direct comparison of the analytical statistics in the last 10 columns of the output file, representing the first third of records in the input file.

The software may also operate on a Windows-based version of Visual Basic, or (ideally) Java based version. Furthermore, a record-by-record evaluation for missing data can be inserted readily at the time variables are permuted or at the time the permutation of variables is evaluated, with missing fields rejected from analysis instead of interpreted as zero. Also, the programming may utilize a more powerful statistical test, quaternary and higher-level indexing, and a user-friendly front end.

The test data is presented in two formats, an Excel spreadsheet (input.xls) and a comma-delimited text file (input.csv). It should be remembered that input.csv is normally copied to the root directory of the c: drive for the program to detect it (regardless of which directory the program itself resides in). Input.xls contains three worksheets. The first spreadsheet includes the formulas used to build the array of mock data. "Constants" at the bottom rows and right hand column of the spreadsheet are random numbers defining certain parameters used to calculate the "data". These include the likelihood of impact of Outcome 1 on a "gene", the likelihood of constitutive expression of a "gene", the amplitude of impact of Outcome 1 on "gene expression", the amplitude of impact of constitutive expression on "gene expression", and the overall expression level noted in an "experiment". The second spreadsheet includes only the "data" calculated from formulas using the "constants" on the first spreadsheet, and normalized to a z score within each field. On the third spreadsheet, the numbers from the second spreadsheet have been frozen as fixed values. This third spreadsheet should correspond exactly to the numbers found in input.csv. The first column includes a randomly assigned value for outcome (1 or 2) and the first row contains field names (gene1 through gene254). The formula in the first worksheet of input.xls reveals explicitly how the "data" are calculated, but the critical assumptions may be summarized. There is a 1% risk of disease-specific expression per gene, 10% risk of constitutive expression per gene, and the impact of disease-specific or constitutive expression is up to four-fold higher than background (evenly distributed from 0 to 4).

In regards to test output, in order to save time, the program may be interrupted before a full set of permutations is complete. (This is done using <ctrl><break>). The output.csv file contains the field headers for the software output, which should be preserved. The numbers below the field headers summarize the statistical data for various permutations of variables and cutpoints, which are found to have a statistically significant association with the output variable. In order to test the program, the numbers should be erased, the file saved (as a .csv file) with the headers only, and the program ran again.

In regards to running the program, Qbasic.exe can be invoked from the DOS command line or from Windows (whence it will open a DOS window). Once Qbasic is invoked, click "File", "Open", "Index3" to open index3.bas, which is the Qbasic program included on the same diskette.

Regarding the validation dataset, valid.xls contains "data" for "expression" of the same "genes" represented in input.csv, but without the outcome field. Instead, the first column contains a record number to be used in cross-referencing. I have the same dataset, but with values filled in for the outcome.

To accomplish validation, copy input.csv and output.csv from the diskette to the root directory. Run index 3 in Qbasic. (In order to do so, the user needs to know that input.csv has 150 rows, excluding the header, and 255 columns, including the outcome variable). If the user does not wish to wait for complete computation, it is possible to use <Ctrl><break> to stop the program once an individual observes some numbers higher than zero in the last column of on-screen output. Next an individual may open output.csv in Excel, select records where the last column is >4, and note the criteria described in the first nine columns. These criteria may be utilized to identify the Outcome value among the records in valid.xls.

The following is an example of an embodiment of the source code which may be utilized in the present invention. It should be noted that the following example is illustrative and not restrictive. Many variations of the code will become apparent to those of skill in the upon review.

```
This program accepts input from c:\input.csv,
'       which should be a comma-delimited text file
'       with field (variable) names in the first row
'       and an outcome field in the first column.
'       Each row should constitute one record.
'       Each outcome field should contain a value of 1 or 2.
'       Each data field should be transformed to a z score (number of
standard deviations off the mean for that field).
'Defines tables for outcome & risk variables, and statistical outcomes:
INPUT "Number of rows (records), excluding header"; rows%
INPUT "Number of columns (fields), including outcome field"; columns
thirds% = (rows% − 1) / 3
DIM outcome%(rows%)                         'outcome data (1 or 2)
DIM table(rows%, 3)                         'risk data (var1, var2, var3) as z scores
DIM stat(10, 8)                             'statistics for last third of records
DIM stat1(10, 8)                            'statistics for mid third of records
DIM stat2(10, 8)                            'statistics for first third of records
DIM field$(columns)                         'field names
'imports row headers from first row of data as field names
OPEN "c:\input.csv" FOR INPUT AS #1
    FOR column = 1 TO columns
    INPUT #1, field$(column)
    'PRINT field$(column)
    'INPUT x
    NEXT column
'imports outcome variable (value = 1 or 2) from 1st column of data into
outcome%
FOR row = 1 TO rows%
    INPUT #1, outcome%(row)
    '  PRINT row; outcome%(row)
        FOR column = 2 TO columns
        INPUT #1, x
        NEXT column
NEXT row
CLOSE #1
    'This section extracts appropriate data into a three-column table with
each combination of variables, a very inefficient process.
    'The entire dataset might be read at once with a program that used more
RAM. Qbasic is limited to 640k.
    FOR var1 = 2 TO (columns − 2)
        FOR var2 = (var1 + 1) TO (columns − 1)
        FOR var3 = (var2 + 1) TO columns
        OPEN "c:\input.csv" FOR INPUT AS #1
            FOR column = 1 TO columns
            INPUT #1, x$ 'imports field names from row 1 into dummy variable
            NEXT column
            FOR row = 1 TO rows%
            ' inputs variable 1
                FOR column = 1 TO (var1 − 1)
                INPUT #1, x
                NEXT column
            INPUT #1, table(row, 1)
            ' inputs variable 2
```

```
            IF var2 = var1 + 1 GOTO in2
              FOR column = (var1 + 1) TO (var2 - 1)
              INPUT #1, x
              NEXT column
in2:
            INPUT #1, table(row, 2)
            ' inputs variable 3
            IF var3 = (var2 + 1) GOTO in3
              FOR column = (var2 + 1) TO (var3 - 1)
              INPUT #1, x
              NEXT column
in3:
            INPUT #1, table(row, 3)
            IF var3 = columns GOTO newvar1
              FOR column = (var3 + 1) TO columns
              INPUT #1, x
              NEXT column
newvar1:
            'PRINT row; outcome%(row), table(row, 1), table(row, 2), table(row, 3)
            'INPUT x
            NEXT row
          CLOSE #1
          FOR ctpt1 = -1.5 TO 1.5 STEP .3
            FOR ctpt2 = -1.5 TO 1.5 STEP .3
              FOR ctpt3 = -1.5 TO 1.5 STEP .3
              'For a given set of ctpts, establishes 8 2 x 2 tables within stat,
              'using only the last 250 rows of data from table
                FOR i = 1 TO 10
                  FOR j = 1 TO 8
                  stat(i, j) = 0
                  NEXT j
                NEXT i
                FOR i = (rows% - thirds%) TO rows%
                risk = 0
                IF table(i, 1) < ctpt1 THEN risk = risk + 100 ELSE risk = risk +
200
                IF table(i, 2) < ctpt2 THEN risk = risk + 10 ELSE risk = risk + 20
                IF table(i, 3) < ctpt3 THEN risk = risk + 1 ELSE risk = risk + 2
                IF risk = 111 THEN risk = 1
                IF risk = 112 THEN risk = 2
                IE risk = 121 THEN risk = 3
                IF risk = 122 THEN risk = 4
                IF risk = 211 THEN risk = 5
                IF risk = 212 THEN risk = 6
                IF risk = 221 THEN risk = 7
                IF risk = 222 THEN risk = 8
                  FOR r = 1 TO 8
                  IF risk = r AND outcome%(i) = 1 THEN stat(1, r) = stat(1, r) + 1
                  IF risk = r AND outcome%(i) = 2 THEN stat(2, r) = stat(2, r) + 1
                  IF risk <> r AND outcome%(i) = 1 THEN stat(3, r) = stat(3, r) + 1
                  IF risk <> r AND outcome%(i) = 2 THEN stat(4, r) = stat(4, r) + 1
                  'PRINT i, r, stat(1, r), stat(2, r), stat(3, r), stat(4, r)
                  NEXT r
                NEXT i
                'PRINT stat(1, 1); stat(2, 1); stat(3, 1); stat(4, 1)
                'statistical testing of the 2 x 2 tables created above
                  FOR r = 1 TO 8
                  'defines relative risk in row 5 of stat
rr:
                IF stat(1, r) = 0 THEN stat(5, r) = 0: GOTO chi
                IF stat(3, r) = 0 THEN stat(5, r) = 99: GOTO chi
                stat(5, r) = ((stat(1, r) / (stat(1, r) + stat(2, r)))) / (stat(3,
r) / (stat(3, r) + stat(4, r)))
                'defines chi-square in 10th row of stat
                "    -- defines chi-square 0 if any expected value < 5
                "    -- bypasses validation and output if chi-square<4
                'NOTE:  Fisher's or (better) Boschloo's test is more appropriate
than chi-square, but for this model program I am using the simpler test
chi:
                e1 = (stat (1, r) + stat (2, r)) * (stat (1, r) + stat (3, r)) /
(stat(1, r) + stat(2, r) + stat(3, r) + stat(4, r))
                IF e1 < 5 GOTO nochi
                e2 = (stat(2, r) + stat (1, r)) * (stat (2, r) + stat (4, r)) /
(stat(1, r) + stat(2, r) + stat(3, r) + stat(4, r))
                IF e2 < 5 GOTO nochi
                e3 = (stat(3, r) + stat(4, r)) * (stat(3, r) + stat(1, r)) /
(stat(1, r) + stat(2, r) + stat(3, r) + stat(4, r))
                IF e3 < 5 GOTO nochi
                e4 = (stat(4, r) + stat(3, r)) * (stat(4, r) + stat(2, r)) /
```

-continued

```
              (stat(1, r) + stat(2, r) + stat(3, r) + stat(4, r)
                   IF e4 < 5 GOTO nochi
                   stat(10, r) = ((stat(1, r) - e1) ^ 2) / e1
                   stat(10, r) = stat(10, r) + ((stat(2, r) - e2) ^ 2) / e2
                   stat(10, r) = stat(10, r) + ((stat(3, r) - e3) ^ 2) / e3
                   stat(10, r) = stat(10, r) + ((stat(4, r) - e4) ^ 2) / e4
                   IF stat(10, r) < 3.9 GOTO nochi
                   hits = hits + 1
                   'defines positive predictive value in 6th row of stat
ppv:
                   IF stat(1, r) + stat(2, r) = 0 THEN stat(6, r) = 0: GOTO nochi
                   stat (6, r) = (stat (1, r) / (stat (1, r) + stat (2, r))
                   'defines negative predictive value in 7th row of stat
npv:
                   IF stat(3, r) + stat(4, r) = 0 THEN stat(7, r) = 0: GOTO nochi
                   stat(7, r) = stat(4, r) / (stat(3, r) + stat(4, r))
                   'defines sensitivity in 8th row of stat
sens:
                   IF stat(1, r) + stat(3, r) = 0 THEN stat(8, r) = 0: GOTO nochi
                   stat(8, r) = stat(1, r) / (stat(1, r) + stat(4, r))
                   'defines specificity in 9th row of stat
spec:
                   IF stat(4, r) + stat(2, r) 0 THEN stat(9, r) = 0: GOTO nochi
                   stat(9, r) = stat(4, r) / (stat(4, r) + stat(2, r)
                   'INPUT "Press any key"; key$
stat1:
                   'validates against later time series
                   'For a given set of ctpts, establishes 8 2 × 2 tables within stat1,
                   'using only the middle 250 rows of data from table
                       FOR i = 1 TO 4
                          FOR j = 1 TO 8
                             stat1(i, j) = 0
                          NEXT j
                       NEXT i
                   'PRINT thirds% + 1; rows% - thirds% - 1
                   FOR i = (thirds% + 1) TO (rows% - thirds% - 1)
                       risk1 = 0
                       IF table(i, 1) < ctpt1 THEN risk1 = risk1 + 100 ELSE risk1 = risk1
+ 200
                       IF table(i, 2) < ctpt2 THEN risk1 = risk1 + 10 ELSE risk1 = risk1
+ 20
                       IF table(i, 3) < ctpt3 THEN risk1 = risk1 + 1 ELSE risk1 = risk1 +
2
                       IF risk1 = 111 THEN risk1 = 1
                       IF risk1 = 112 THEN risk1 = 2
                       IF risk1 = 121 THEN risk1 = 3
                       IF risk1 = 122 THEN risk1 = 4
                       IF risk1 = 211 THEN risk1 = 5
                       IF risk1 = 212 THEN risk1 = 6
                       IF risk1 = 221 THEN risk1 = 7
                       IF risk1 = 222 THEN risk1 = 8
                       IF risk1 = r AND outcome%(i) = 1 THEN stat1(1, r) = stat1(1, r) +
1
                       IF risk1 = r AND outcome%(i) = 2 THEN stat1(2, r) = stat1(2, r) +
1
                       IF risk1 <> r AND outcome%(i) = 1 THEN stat1(3, r) = stat1(3, r) +
1
                       IF risk1 <> r AND outcome%(i) = 2 THEN stat1(4, r) = stat1(4, r) +
1
                       NEXT i
                   'defines relative risk in row 5 of stat1
rr1:
                   IF stat1(1, r) = 0 THEN stat1(5, r) = 0: GOTO checkrr1
                   IF stat1(3, r) + stat1(4, r) = 0 THEN stat1(5, r) = 99: GOTO
checkrr1
                   stat1(5, r) = ((stat1(1, r) / (stat1(1, r) + stat1(2, r))) /
stat1(3, r) / (stat1(3, r) + stat1(4, r))
checkrr1:
                   IF stat1(5, r) < 1 AND stat1(5, r) > 1 THEN GOTO nochi
                   IF stat1(5, r) > 1 AND stat1(5, r) < 1 THEN GOTO nochi
                   'defines chi-square in 10th row of stat1
                   '  -- defines chi-square 0 if any expected value < 5
                   'NOTE:  Fisher's or (better) Boschloo's test is more appropriate
than chi-square, but for this model program I am using the simpler test
chi1:
                   e1 = (stat1(1, r) + stat1(2, r)) + (stat1(1, r) + stat1(3, r)) /
(stat1(1, r) + stat1(2, r) + stat1(3, r) + stat1(4, r))
                   IF e1 < 5 GOTO nochi
                   e2 = (stat1(2, r) + stat1(1, r)) * (stat1(2, r) + stat1(4, r)) /
```

-continued

```
                  (stat1(1, r) + stat1 (2, r) + stat1 (3, r) + stat1 (4, r)
                  IF e2 < 5 GOTO nochi
                  e3 = (stat1(3, r) + stat1(4, r)) * (stat1(3, r) + stat1(1, r)) /
(stat1(1, r) + stat1(2, r) + stat1(3, r) + stat1(4, r))
                  IF e3 < 5 GOTO nochi
                  e4 = (stat1(4, r) + stat1(3, r)) * (stat1(4, r) + stat1(2, r)) /
(stat1(1, r) + stat1(2, r) + stat1(3, r) + stat1(4, r))
                  IF e4 < 5 GOTO nochi
                  stat1(10, r) = ((stat1(1, r) - e1) ^ 2) / e1
                  stat1(10, r) = stat1(10, r) + ((stat1(2, r) - e2) ^ 2) / e2
                  stat1(10, r) = stat1(10, r) + ((stat1(3, r) - e3) ^ 2) / e3
                  stat1(10, r) = stat1(10, r) + ((stat1(4, r) - e4) ^ 2) / e4
                  IF stat1(10, r) < 3.9 GOTO nochi
                  hits1 = hits1 + 1
                  'defines positive predictive value in 6th row of stat1
ppv1:
                  IF stat1(1, r) + stat1(2, r) = 0 THEN stat1(6, r) = 0: GOTO npv1
                  stat1(6, r) = (stat1(1, r) / (stat1(1, r) + stat1(2, r)))
                  'defines negative predictive value in 7th row of stat1
npv1:
                  IF stat1(3, r) + stat1(4, r) = 0 THEN stat1(7, r) = 0: GOTO sens1
                  stat1(7, r) = stat1(4, r) / (stat1(3, r) + stat1(4, r))
                  IF ((stat1(6, r) - .5) * (stat(6, r) - .5) < 0 AND (stat(7, r) -
.5) * (stat1(7, r) - .5) < 0) THEN GOTO nochi
                  'defines sensitivity in 8th row of stat1
sens1:
                  IF stat1(1, r) + stat1(3, r) = 0 THEN stat1(8, r) = 0: GOTO nochi
                  stat1 (8, r) = stat1 (1, r) / (stat1(1, r) + stat1(4, r)
                  'defines specificity in 9th row of stat1
spec1:
                  IF stat1(4, r) + stat1(2, r) = 0 THEN stat1(9, r) = 0: GOTO nochi
                  stat1(9, r) = stat1(4, r) / (stat1(4, r) + stat1(2, r))
stat2:
                  'validates against later time series
                  'For a given set of ctpts establishes 8 2 x 2 tables within stat2,
                  'using only the top 250 rows of data from table
                     FOR i = 1 TO 4
                        FOR j = 1 TO 8
                          stat2(i, j) = 0
                        NEXT j
                     NEXT i
                     FOR i = 1 TO thirds%
                     risk2 = 0
                     IF table(i, 1) < ctpt1 THEN risk2 = risk2 + 100 ELSE risk2 = risk2
+ 200
                     IF table(i, 2) < ctpt2 THEN risk2 = risk2 + 10 ELSE risk2 = risk2
+ 20
                     IF table(i, 3) < ctpt3 THEN risk2 = risk2 + 1 ELSE risk2 = risk2 +
2
                     IF risk2 = 111 THEN risk2 = 1
                     IF risk2 = 112 THEN risk2 = 2
                     IF risk2 = 121 THEN risk2 = 3
                     IF risk2 = 122 THEN risk2 = 4
                     IF risk2 = 211 THEN risk2 = 5
                     IF risk2 = 212 THEN risk2 = 6
                     IF risk2 = 221 THEN risk2 = 7
                     IF risk2 = 222 THEN risk2 = 8
                     IF risk2 = r AND outcome%(i) = 1 THEN stat2(1, r) = stat2(1, r) +
1
                     IF risk2 = r AND outcome%(i) = 2 THEN stat2(2, r) = stat2(2, r) +
1
                     IF risk2 <> r AND outcome%(i) = 1 THEN stat2(3, r) = stat2(3, r) +
1
                     IF risk2 <> r AND outcome%(i) = 2 THEN stat2(4, r) = stat2(4, r) +
1
                     NEXT i
                     'defines relative risk in row 5 of stat2
rr2:
                     IF stat2(1, r) = 0 THEN stat2(5, r) = 0: GOTO checkrr2
                     IF stat2(3, r) + stat2(4, r) = 0 THEN stat2(5, r) = 99: GOTO
checkrr2
                     stat2(5, r) = ((stat2(1, r) / (stat2(1, r) + stat2(2, r)))) /
(stat2(3, r) / (stat2(3, r) + stat2(4, r)))
checkrr2:
                     IF stat2(5, r) < 1 AND stat(5, r) > 1 THEN GOTO nochi
                     IF stat2(5, r) > 1 AND stat(5, r) < 1 THEN GOTO nochi
                     'defines chi-square in 10th row of stat2
                     ' -- defines chi-square = 0 if any expected value < 5
                     'NOTE: Fisher's or (better) Boschloo's test is more appropriate
```

-continued than chi-square, but for this model program I am using the simpler test
chi2:

e1 = (stat2(1, r) + stat2(2, r)) + (stat2(1, r) + stat2(3, r)) / (stat2(1, r) + stat2(2, r) + stat2(3, r) + stat2(4, r))
    IF e1 < 5 GOTO nochi
e2 = (stat2(2, r) + stat2(1, r)) + (stat2(2, r) + stat2(4, r)) / (stat2(1, r) + stat2(2, r) + stat2(3, r) + stat2(4, r))
    IF e2 < 5 GOTO nochi
e3 = (stat2(3, r) + stat2(4, r)) * (stat2(3, r) + stat2(1, r)) / (stat2(1, r) + stat2(2, r) + stat2(3, r) + stat2(4, r))
    IF e3 < 5 GOTO nochi
e4 = (stat2(4, r) + stat2(3, r)) * (stat2(4, r) + stat2(2, r)) / (stat2(1, r) + stat2(2, r) + stat2(3, r) + stat2(4, r))
    IF e4 < 5 GOTO nochi
    stat2(10, r) = ((stat2(1, r) − e1) [001b]^ 2) / e1
    stat2(10, r) = stat2(10, r) + ((stat2(2, r) − e2) ^ 2) / e2
    stat2(10, r) = stat2(10, r) + ((stat2(3, r) − e3) ^ 2) / e3
    stat2(10, r) = stat2(10, r) + ((stat2(4, r) − e4) ^ 2) / e4
    IF stat2(10, r) < 3.9 GOTO nochi
    hits2 = hits2 + 1
    'defines positive predictive value in 6th row of stat2 ppv2:

IF stat2(1, r) + stat2(2, r) = 0 THEN stat2(6, r) = 0: GOTO npv2
    stat2(6, r) = (stat2(1, r) / (stat2(1, r) + stat2(2, r)))
    'defines negative predictive value in 7th row of stat2 npv2:

IF stat2(3, r) + stat2(4, r) = 0 THEN stat2(7, r) = 0: GOTO sens2
    stat2(7, r) = stat2(4, r) / (stat2(3, r) + stat2(4, r))
    IF ((stat2(6, r) − .5) * (stat6, r) − .5) < 0 AND (stat7, r) − .5) * (stat2(7, r) − *5) < 0) THEN GOTO nochi
    'defines sensitivity in 8th row of stat2 sens2:

IF stat2(1, r) + stat2(3, r) = 0 THEN stat2(8, r) = 0: GOTO spec2
    stat2(8, r) = stat2(1, r) / (stat2(1, r) + stat2(4, r))
    'defines specificity in 9th row of stat2 spec2:

IF stat2(4, r) + stat2(2, r) = 0 THEN stat2(9, r) = 0: GOTO outputs
    stat2(9, r) = stat2(4, r) / (stat2(4, r) + stat2(2, r))

outputs:

hits1 = hits1 + 1
    IF r = 1 THEN
      r1$ = "<"
      r2$ = "<"
      r3$ = "<"
      GOTO openfile
    END IF
    IF r = 2 THEN
      r1$ = "<"
      r2$ = "<"
      r3$ = ">"
      GOTO openfile
    END IF
    IF r = 3 THEN
      r1$ = "<"
      r2$ = ">"
      r3$ = "<"
      GOTO openfile
    END IF
    IF r = 4 THEN
      r1$ = "<"
      r2$ = ">"
      r3$ = ">"
      GOTO openfile
    END IF
    IF r = 5 THEN
      r1$ = ">"
      r2$ = "<"
      r3$ = "<"
      GOTO openfile
    END IF
    IF r = 6 THEN
      r1$ = ">"
      r2$ = "<"
      r3$ = ">"
      GOTO openfile
    END IF
    IF r = 7 THEN
      r1$ = ">"
      r2$ = ">"

-continued

```
                r3$ = "<"
                GOTO openfile
            END IF
            IF r = 8 THEN
                r1$ = ">"
                r2$ = ">"
                r3$ = ">"
                GOTO openfile
            END IF
openfile:
                OPEN "c:\output.csv" FOR APPEND AS #2
                writes = writes + 1
                WRITE #2, field$(var1), r1$, ctpt1, field$(var2), r2$, ctpt2,
field$(var3), r3$, ctpt3, stat(1, r), stat(2, r), stat(3, r), stat(4, r),
stat(5, r), stat(6, r), stat(7, r), stat(8, r), stat(9, r), stat(10, r),
stat1(1, r), stat1(2, r), stat1(3, r), stat1(4, r), stat1(5, r), stat1(6,
r), stat1(7, r), stat1(8, r), stat1(9, r), stat1(10, r), stat2(1, r),
stat2(2, r), stat2(3, r), stat2(4, r), stat2(5, r), stat2(6, r), stat2(7,
r), stat2(8, r), stat2(9, r), stat2(10, r)
                CLOSE #2
                'PRINT "ctpts: ", ctpt1, ctpt2, ctpt3, r
                'PRINT "RR, PPV, NPV:", stat(5, r), stat(6, r), stat(7, r)
                'PRINT "Sensitivity=", stat(8, r), " Specificity=", stat(9, r)
                'PRINT stat(1, r), stat(2, r), stat(3, r), stat(4, r), stat(10, r)
                'INPUT "Press any key (2)"; key$
nochi:
                stat(10, r) = 0
                'PRINT ctpt1, ctpt2, stat(10, r)
            NEXT r
        IF ctpt3 < -1.5 THEN ctpt3 = -1.5
        NEXT ctpt3
      IF ctpt2 < -1.5 THEN ctpt2 = -1.5
      NEXT ctpt2
      PRINT ctpt1; var1; var2; var3; hits; hits1; writes; hits2
      'PRINT stat(1, 1), stat(2, 1), stat(3, 1), stat(4, 1)
    IF ctpt1 < -2 THEN ctpt1 = -2
    NEXT ctpt1
  NEXT var3
 NEXT var2
NEXT var1
```

In summary, diagnosis based on gene expression depends on massively parallel data analysis. In one embodiment it is shown that six 15-base two-nucleotide subsets contain matches to over two-thirds of all human genes and, more than a third of prokaryotic genes. Over two-thirds of genes matched by these oligonucleotides have one or more specific matches. In most circumstances, the diagnostic target would be the human genome. The human genome has at least 100,000 genes, of which approximately 10 percent are expressed in a particular tissue at a particular time. A human gene database used in an embodiment of the present invention contained 2,736 nonredundant genes, comparable in complexity to the gene expression repertoire of a typical eukaryotic cell. Approximately one percent of expressed genes—some one hundred genes in a human cell—are likely to be expressed differentially in response to deformed stimuli. The present invention shows that a diagnostic platform based on a single oligonucleotide subset would identify at least 30 of these 100 genes specifically. Since hybridization to specific loci on solid-phase supports can be measured as floating-point variables, the transcriptional activity of each matching gene can be interpreted quantitatively in relationship to all the others. The power of this platform to detect and discriminate among a multitude of diseases is therefore immense. This power is increased when one uses multiple oligonucleotide subsets, and will increase still further with improvements in the ability to make and analyze larger oligonucleotide arrays.

In addition to massive parallelism, gene detection strategies require low cost if they are to be used broadly for clinical diagnosis. The extraction and amplification techniques required for the template are in common use and well on their way to automation. The oligonucleotides proposed for detection are complex enough to provide detailed information about gene usage, yet simple enough to use routinely. As previously shown, each nucleotide subset can be synthesized and analyzed on solid supports by a variety of existing techniques. Since these particular subsets comprise only two nucleotides each, the masking protocol for their synthesis is quite straightforward, offering the potential for a cheap way of sampling transcriptional activity across the entire genome.

Even qualitative assays for single, well-chosen gene targets can provide convincing diagnostic information in some circumstances. When a single gene is insufficient, arrays of known genes have obvious utility for analyzing transcriptional responses to specific stimuli. It is likely, however, that most disease specific responses involve multiple genes that many of these genes are poorly recognized and that relative rather than absolute levels of transcription often determine outcomes. Pattern recognition by the oligonucleotide subsets allows qualitative, quantitative and relational analysis of genes whose locus, sequence, function or organism may be unknown. Accordingly this method provides a universal platform for diagnosis of most known diseases as well as for gene discovery.

The above description is illustrative and not restrictive. Many variations of the invention will become apparent to those of skill in the art upon review of this disclosure. Therefore, the scope of the invention should, be determined not with reference to the above description, but instead should be determined with reference to the appended claims along with their full scope of equivalents.

What is claimed is:

1. A device for assaying nucleic acids in a sample, the device comprising:

at least one surface and one or more arrays of a plurality of at least 100 different oligomer probes, each comprising an oligomer sequence, being attached to the surface, wherein the length of every oligomer sequence in an array is fixed and each different oligomer sequence has a distinct address on the surface;

wherein the oligomer sequences in the arrays are chosen from the set of all possible combinations of sequences that can be generated from a number of different bases that does not include all four of the bases deoxyadenosine, deoxythymidine, deoxyguanosine, and deoxycytidine, and does not include all four of the bases adenine, uracil, guanine, and cytosine.

2. The device of claim 1 wherein the array consists of every possible combination of sequences that can be generated for the length of the oligomer and the number of different bases that are used.

3. The device of claim 2 wherein the length of the oligomer is 8–35 bases and the number of different bases is two.

4. The device of claim 2 wherein the length of the oligomer is 8–35 bases and the number of different bases is three.

5. The device of claim 1 wherein the different bases are guanine and cytosine.

6. The device of claim 1 wherein the oligomers in the arrays have a length of 12 bases.

7. The device of claim 1 wherein the oligomers in the arrays have a length of 11 to 30 bases.

8. The device of claim 1 wherein the oligomers in the first array have a length of 15 to 20 bases.

9. The device of claim 1 wherein the oligomers in the first array have a length of 15 bases.

10. An array of oligonucleic acid probes immobilized on a solid support for assaying nucleic acids in a sample, said array comprising at least 100 different probes each of 9 to 30 bases in length occupying separate known sites in said array, said oligonucleic acid probes including probes that are chosen from a set of all possible combinations of sequences that may be generated by using a group of different bases; wherein the number of different bases does not include all four of the bases deoxyadenosine, deoxythymidine, deoxyguanosine, and deoxycytidine, and does not include all four of the bases adenine, uracil, guanine, and cytosine.

11. The array of oligonucleic acid probes in claim 15 wherein the number of different bases is two or three bases.

12. The array of oligonucleic acid probes in claim 10 wherein the nucleic acids are nucleosides.

13. The array of oligonucleic acid probes in claim 11 wherein the number of different bases is two, and the different bases are adenine and thymine.

14. An array of oligomers having nucleic acid sequences for assaying nucleic acids in a sample, the array comprising:

a plurality of at least 100 different oligomer probes, immobilized to distinct known sites on a surface, wherein the sequences are fixed in length and the oligomer probes are attached to the surface by a spacer;

wherein the oligomer sequences are chosen from the set of all possible combinations of sequences that can be generated for the total number of bases in the oligomer and the number of different bases that are used; and wherein the number of different bases does not include all four of the bases deoxyadenosine, deoxythymidine, deoxyguanosine, and deoxycytidine, and does not include all four of the bases adenine, uracil, guanine, and cytosine.

15. The array of claim 14 wherein the spacer is less than 100 nanometers in length.

16. The array of claim 14 wherein the spacer is a linear polymer with a molecular weight between 100 and 100,000.

17. The array of claim 16 wherein the linear polymer is poly(ethylene oxide).

18. The array of claim 14 wherein the spacer comprises nucleic acid bases.

19. The array of claim 18 wherein all of the bases are nucleotides.

20. An array for assaying nucleic acids in a sample comprising:

a plurality of at least 100 different nucleic acid oligomer probes comprising sequences immobilized to distinct known sites on a surface wherein the sequences comprise at least one variable portion and at least one fixed portion and the sequences are at least 4 bases in length;

wherein each variable portion comprises oligomer sequences chosen from the set of all possible combinations of sequences that can be generated for the length of the variable portion and the number of different bases in the variable portion, and wherein the number of different bases in the variable portion does not include all four of the bases deoxyadenosine, deoxythymidine, deoxyguanosine, and deoxycytidine, and does not include all four of the bases adenine, uracil, guanine, and cytosine.

21. The array of claim 20 having only one fixed portion and only one variable portion.

22. The array of claim 21 wherein the variable portion is six bases in length and a number of different bases in the variable portion is two or three.

23. The set of arrays of claim 21 wherein the sequences comprise two fixed portions and one variable portion.

24. The set of arrays of claim 23 wherein the variable portion is disposed between two fixed portions, whereby a first fixed portion is affixed to the surface, the variable portion is attached to the first fixed portion, and a second fixed portion is disposed at the unbound end of the sequence.

25. A device for diagnosis of disease in a living organism having oligomers having nucleic acid sequences, the device comprising: an array of a plurality of at least 100 different nucleic acid oligomer probes having sequences immobilized to known distinct sites on a surface, wherein a fraction of the chemically distinct oligomers in the organism that reproducibly hybridize to the oligomer probes attached to the surface is at least one percent and the oligomers in the array are made from a number of different bases tat does not include all four of the bases deoxyadenosine, deoxythymidine, deoxyguanosine, and deoxycytidine, and does not include all four of the bases adenine, uracil, guanine, and cytosine.

26. The device of claim 25 wherein the device immobilizes at least one percent of the total number of chemically distinct species of RNA oligomers that are present in the organism.

27. The device of claim 26 wherein the device immobilizes at least five percent of the total number of chemically distinct RNA oligomers that are present in the organism.

28. The device of claim 25 wherein the fraction of the chemically distinct nucleic acid oligomers in the organism that reproducibly hybridize to a unique position on the surface is at least 30 percent.

29. The device of claim 1 wherein at least one array is interspersed with at least one other array.

30. The array of oligonucleic acid probes in claim 10 wherein the different bases are chosen from the group consisting of adenine, thymine, guanine, cytosine, deoxyadenosine, deoxythymidine, deoxyguanosine, deoxycytidine, and uracil.

* * * * *